United States Patent [19]

Stahl et al.

[11] Patent Number: 5,434,290
[45] Date of Patent: Jul. 18, 1995

[54] PREPARATION OF 5-CYANOVALERATES

[75] Inventors: Stefan Stahl, Worms; Wolfgang Harder, Weinheim; Arthur Hoehn, Ludwigshafen, all of Germany

[73] Assignee: BASF Aktiengesellschaft, Ludwigshafen, Germany

[21] Appl. No.: 203,022

[22] Filed: Feb. 28, 1994

[30] Foreign Application Priority Data

Mar. 3, 1993 [DE] Germany .................. 43 06 507.4

[51] Int. Cl.$^6$ ............................................. C07C 253/30
[52] U.S. Cl. ..................................... 558/353; 558/441
[58] Field of Search .......................................... 558/353

[56] References Cited

U.S. PATENT DOCUMENTS

| | | | |
|---|---|---|---|
| 4,060,543 | 11/1977 | Weitz et al. | 260/464 |
| 4,508,660 | 4/1985 | Sieja | 558/353 |
| 4,933,483 | 6/1990 | Burke et al. | 558/353 |
| 4,950,778 | 8/1990 | Burke et al. | 558/353 |
| 4,960,926 | 10/1990 | Drent | 558/353 X |

FOREIGN PATENT DOCUMENTS

| | | |
|---|---|---|
| 0373579 | 6/1990 | European Pat. Off. |
| 377838 | 7/1990 | European Pat. Off. |
| 1497046 | 1/1978 | United Kingdom . |

*Primary Examiner*—Joseph Paul Brust
*Attorney, Agent, or Firm*—Keil & Weinkauf

[57] ABSTRACT

Preparation of 5-cyanovalerates (I) by the carbonylation of a 1-cyanobutene with carbon monoxide and an alkanol (II) corresponding to the ester radical at an elevated temperature and under superatmospheric pressure in the presence of a cobalt catalyst as well as in the presence of an activating solvent, in which the activating solvent used is an effective amount of a carbonic diester, a carbamate, or a urea of the general formula IIIa, IIIb, or IIIc $$R\!-\!O\!-\!CO\!-\!O\!-\!R \qquad \text{(IIIa)}$$

$$R_2N\!-\!CO\!-\!O\!-\!R \qquad \text{(IIIb)}$$

$$R_2N\!-\!CO\!-\!NR_2 \qquad \text{(IIIc)}$$

or a mixture of these compounds (R's same or different, $C_1$–$C_6$ alkyl, $C_5$–$C_7$ cycloalkyl groups or together form 5-membered to 7-membered rings).

The end products I serve as intermediates, chiefly for the preparation of ϵ-caprolactam.

4 Claims, No Drawings

PREPARATION OF 5-CYANOVALERATES

The present invention relates to an improved process for the preparation of 5-cyanovalerates (I) by the carbonylation of a 1-cyanobutene with carbon monoxide and an alkanol (II) corresponding to the ester radical at an elevated temperature and under superatmospheric pressure in the presence of a cobalt catalyst as well as in the presence of an activating solvent.

According to the general teaching of EP-A 373,579, it is known to be possible to convert 1-cyanobutenes to 5-cyanovaleric acid or to the alkyl esters of these acids by carbonylation with carbon monoxide and water or an alkanol under elevated pressure and temperature conditions using cobalt catalysts, this reaction being carried out in the presence of from 70 to 99 wt %, based on the weight of the reaction mixture, of a lactam or cyclic urea derivative acting as activating solvent. As far as the preparation of the esters is concerned, this reaction is described only with reference to the methyl ester using the lactam N-methylpyrrolidone, but the conversion of 12.9% achieved by this process is unsatisfactory.

It is thus an object of the present invention to make the alkyl esters of 5-cyanovaleric acid more readily available than hitherto. In particular, activating solvents are required which show a favorable action even at a relatively low concentration.

Accordingly, we have found an improved process for the preparation of a 5-cyanovalerate (I) by the carbonylation of a 1-cyanobutene with carbon monoxide and an alkanol (II) corresponding to the ester radical, at an elevated temperature and under superatmospheric pressure in the presence of a cobalt catalyst and in the presence of an activating solvent, wherein the activating solvent used comprises an effective amount of a carbonic diester, a carbamate, or a urea of the general formula IIIa, IIIb, or IIIc

R—O—CO—O—R         (IIIa)

R$_2$N—CO—O—R         (IIIb)

R$_2$N—CO—NR$_2$         (IIIc)

or a mixture of these compounds, in which the radicals R may be the same or different and stand for C$_1$-C$_6$ alkyl groups or C$_5$-C$_7$ cycloalkyl groups, which radicals can be interconnected to form 5-membered to 7-membered rings. The reaction can be illustrated as follows:

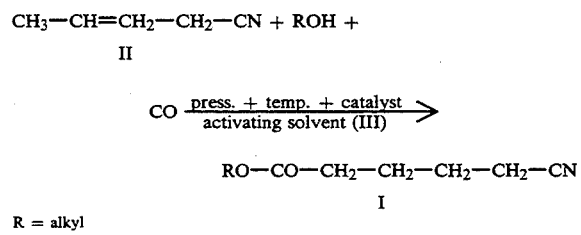

The 1-ene and 3-ene isomer or, if desired, isomer mixtures can be used instead of cyanobut-2-ene, since the isomers assume a state of equilibrium under the reaction conditions. Also, both the trans- and cis-isomers of cyanobut-1-ene and cyanobut-2-ene are suitable for use as starting compounds for the process of the invention. For economical reasons, it is preferred to use cyanobut-2-ene, which is readily obtainable by adding hydrogen cyanide to butadiene.

The success of the process of the invention is not basically dependent on the alkanols ROH (II). Thus C$_1$-C$_2$ alkanols are suitable, of which C$_1$-C$_4$ alkanols are preferred, especially methanol and ethanol.

For each mole of 1-cyanobutene there will normally be used from 0.5 to 10 mol and preferably from 1 to 5 mol of the alkanol II. Substoichiometric amounts of alkanol are recommendable when the conversion of the cyanobutene should be restricted in order, for example, to raise the selectivity toward the desired end product (I).

An essential feature of the process of the invention is the co-use of one of the activating solvents IIIa to IIIc defined above,

R—O—CO—O—R         (IIIa)

R$_2$N—CO—O—R         (IIIb)

R$_2$N—CO—NR$_2$         (IIIc)

in which the radicals R can be the same or different and stand for C$_1$-C$_6$ alkyl groups or C$_5$-C$_7$ cycloalkyl groups, which radicals can be interconnected to form 5-membered to 7-membered rings.

Suitable carbonic diesters IIIa are preferably symmetrical esters, such as dimethyl carbonate and diethyl carbonate. Cyclic carbonates are particularly preferred, such as ethylene carbonate, 1,2-propylene carbonate, 1,3-propylene carbonate, and 1,2-isobutylene carbonate.

Suitable carbamates IIIb are preferably butyl N,N-dimethyl carbamate and butyl N,N-diethyl carbamate as well as, primarily, cyclic esters such as 3-methyl-2-oxazolidinone, 3-ethyl-2-oxazolidinone, 3-propyl-2-oxazolidinone, 3-butyl-2-oxazolidinone, 3-pentyl-2-oxazolidinone, 3,4-dimethyl-2-oxazolidinone, 3,5-dimethyl-2-oxazolidinone, 3-methyl-4-ethyl-2-oxazolidinone, and 3-ethyl-5-methyl-2oxazolidinone.

Suitable ureas IIIc are cyclic urea derivatives such as N,N'-dimethylethylene urea, N,N'-diethylethylene urea, and N,N'-dimethylpropylene urea as well as, primarily, open-chained compounds such as N,N,N',N'-tetramethyl urea and N,N,N',N'-tetraethyl urea.

The amount used of activating solvent or, if used, mixtures of these activating solvents is usually arbitrary. The amounts used are preferably kept to a minimum. The initial concentration of the activating solvents in the total reaction mixture can be from 20 to 85 wt % and preferably from 30 to 75 wt% and more preferably from 35 to 65 wt%.

Above said range, there are obtained mostly good selectivities toward the straight-chain 5-cyanovalerates, but this is at the expense of a reduction of the space-time yield of the reaction and the cost of purification increases.

The reaction can alternatively be carried out in the presence of further organic solvents, provided they are inert under the reaction conditions. For example, hydrocarbons are suitable such as n-pentane, n-hexane, toluene, and the xylenes, in addition to ethers, eg, tetrahydrofuran, dioxane, or ethylene glycol dimethyl ether, as well as carboxylates such as methyl acetate, ethyl acetate, and butyl acetate.

In other respects, the carbonylation is carried out in conventional manner, ie, at temperatures ranging from 130° to 200° C. and preferably from 140° to 190° C. and under a pressure of from 50 to 700 bar and preferably from 100 to 350 bar. Preferably, pure carbon monoxide is used for the reaction, but the presence of hydrogen, in a concentration which should be lower than 10 vol %, depending on the particular embodiment of the process of the invention, can also effect activation of the cobalt catalyst.

Suitable cobalt catalysts are dicobalt octacarbonyl or cobalt carbonyl hydrogen.

Instead of these carbonyl complexes it is also possible to use salts such as cobalt acetate, cobalt formate, or cobalt-2-ethyl hexanoate, but most preferably the cobalt salts of those carboxylic acids which can be produced in minor quantities during the reaction as by-products, such as, for example, cobalt valerate, cobalt adipate, or cobalt methyl glutarate. These salts convert to the active complexes under the reaction conditions in situ.

The concentration of the catalysts is usually from 0.1 to 5 wt % and preferably from 0.3 to 3 wt % of cobalt, based on the total weight of the reaction mixture.

The formation of a catalytically effective cobalt compound can be accelerated by the addition of water, preferably used in an amount of from 0.5 to 4 too per mole of cobalt.

The process may be carried out batchwise or continuously by conventional techniques.

To achieve satisfactory selectivities toward the end product I the reaction is preferably carried out up to a conversion of from 35 to 70%, based on the 1-cyanobutene.

The purification of the reaction mixture is carried out in known manner, preferably by fractional distillation. The solvents and starting compounds thus obtained are advantageously recycled to the carbonylation.

The linear cyanates are usually obtained in selectivities of from 80 to 90%, based on 50% conversion of the 1-cyanobutene. There are also formed approximately from 0.5 to 5% chiefly of dialkyl adipates derived from the alkanols II, and from 0.5 to 8% of valeronitrile as well as small amounts of other by-products.

The process of the invention has the advantage that even when use is made of relatively small amounts of the said activating solvents IIIa to IIIc surprisingly high selectivities toward the straight-chain 5-cyanovalerates (I) are achieved.

The esters of 5-cyanovaleric acid produced by the method of the invention are precursors for ε-caprolactam which is of significance in the preparation of polyamides.

EXAMPLES

Example 1

An autoclave having a capacity of 107 mL was filled with a solution of

| |
|---|
| 27.2 wt % of 1-cyanobut-2-ene |
| 21.2 wt % of methanol |
| 48.2 wt % of N,N,N',N'-tetramethylurea |
| 2.8 wt % of $Co_2(CO)_8$, and |
| 0.6 wt % of water. |

10.3 g/h of the same solution and 1.72 L/h (STP) of carbon monoxide gas were then continuously added under a co pressure of approximately 200 bar and at a temperature of 160° C. and the continuously discharged effluent was subjected to gas-chromatographic analysis (internal standard benzonitrile).

The following results were achieved (GC):
conversion of the cyanobutene: 47%
selectivity toward cyanates: 89%
-proportion thereof toward I (n-portion): 98%

The effluent was worked up by distillation in the usual manner.

Example 2

The experiment was carried out in a manner similar to Example 1, except that 8,9 g/h of a solution of

| |
|---|
| 27.2 wt % of 1-cyanobut-2-ene |
| 21.2 wt % of methanol |
| 48.2 wt % of N,N'-dimethylpropylene urea |
| 2.8 wt % of $Co_2(CO)_8$, and |
| 0.6 wt % of water | and 1.72 L/h (STP) of carbon monoxide gas were caused to react. The following results were achieved (GC):
conversion of the cyanobutene: 39%
selectivity toward cyanates: 89%
-proportion thereof toward I (n-portion): 96%

Example 3

The experiment was carried out in a manner similar to Example 1, except that 9.6 g/h of a solution of

| |
|---|
| 27.0 wt % of 1-cyanobut-2-ene |
| 21.3 wt % of methanol |
| 48.4 wt % of 3-methyl-2-oxazolidinone |
| 2.8 wt % of $Co_2(CO)_8$ and |
| 0.5 wt % of water | and 1.68 L/h (STP) of carbon monoxide gas were caused to react. The following results were achieved (GC):
conversion of the cyanobutene: 57%
selectivity toward cyanates: 93%
-proportion thereof toward I (n-portion): 96%

Example 4

The experiment was carried out in a manner similar to Example 1, except that 8.8 g/h of a solution of

| |
|---|
| 16.0 wt % of 1-cyanobut-2-ene |
| 12.5 wt % of methanol |
| 69.5 wt % of propylene carbonate |
| 1.7 wt % of $Co_2(CO)_8$ and |
| 0.3 wt % of water | and 1.68 L/h (STP) of carbon monoxide gas were caused to react. The following results were achieved (GC):
conversion of the cyanobutene: 63%
selectivity toward cyanates: 93%
-proportion thereof toward I (n-portion): 95%

Example 5

CO was pumped into an autoclave containing 120 g of a solution of

| |
|---|
| 27.0 wt % of 1-cyanobut-2-ene |
| 21.3 wt % of methanol |
| 48.4 wt % of 3-butyl-2-oxazolidinone |

| |
|---|
| 2.8 wt % of Co₂(CO)₈ and |
| 0.5 wt % of water | under a pressure of 100 bar, after which the reaction mixture was heated to 160° C. The pressure was then raised to 210 bar by forcing in more carbon monoxide and the reaction mixture was kept at 160° C. for 6 h. The effluent was subjected to gas-chromatographic analysis as described above.

The following results were achieved (GC):
conversion of the cyanobutene: 44%
selectivity toward cyanates: 88%
-proportion thereof toward I (n-portion): 94%

The effluent was then worked up by distillation in the usual manner.

Example 6

The experiment was carried out as described in Example 5. The reaction time was 4 h.

There were used 120 g of a solution of

| |
|---|
| 27.0 wt % of 1-cyanobut-2-ene |
| 21.3 wt % of methanol |
| 48.4 wt % of 3-methyl-2-oxazolidinone |
| 2.8 wt % of Co₂(CO)₈ and |
| 0.5 wt % of water. |

The following results were achieved (GC):
conversion of the cyanobutene: 66%
selectivity toward cyanates: 93%
-proportion thereof toward I (n-portion): 96%

Example 7

320 g of a solution of

| |
|---|
| 27.2 wt % of 1-cyanobut-2-ene |
| 21.2 wt % of methanol |
| 48.2 wt % of 3-methyl-2-oxazolidinone |
| 2.8 wt % Of Co₂(C)₈ and |
| 0.6 wt % of water | were fed to an autoclave at a temperature of 160° C. and under a CO pressure of 30 bar and were subjected to the carbonylation reaction in the autoclave at the same temperature and under a CO pressure of 270 bar for 4 h.

The effluent was subjected to gas-chromatographic analysis as described above.

The following results were achieved (GC):
conversion of the cyanobutene: 53%
selectivity toward cyanates: 90%
-proportion thereof toward I (n-portion): 96%

We claim:

1. A process for the preparation of a 5-cyanovalerate (I) by the carbonylation of a 1-cyanobutene with carbon monoxide and a $C_1$–$C_{12}$-alkanol (II) corresponding to the ester radical, at a temperature of from 130° to 200° C. and under superatomospheric pressure in the presence of a cobalt catalyst selected from the group consisting of dicobalt octacarbonyl, cobalt carbonyl hydrogen, cobalt acetate, cobalt formate, cobalt-2-ethyl hexanoate, cobalt valerate, cobalt adipate and cobalt methyl glutarate and in the presence of an activating solvent of the formula (IIIa)

$$R\text{—}O\text{—}CO\text{—}O\text{—}R \qquad (IIIa)$$

in which the R radicals are $C_1$–$C_6$-alkyl groups that are interconnected to form a cyclic carbonate having a 5-membered to 7-membered ring, the initial concentration of the activating solvent in the total reaction mixture being from 20 and 85 wt. %.

2. The process claim 1, wherein the alkanol (II) used is methanol or ethanol.

3. A process for the preparation of a 5-cyanovalerate (I) by the carbonylation of a 1-cyanobutene with carbon monoxide and a $C_1$–$C_{12}$-alkanol (II) corresponding to the ester radical, at a temperature of from 130° to 200° C. and under superatomospheric pressure in the presence of a cobalt catalyst selected from the group consisting of dicobalt octacarbonyl, cobalt carbonyl hydrogen, cobalt acetate, cobalt formate, cobalt-2-ethyl hexanoate, cobalt valerate, cobalt adipate and cobalt methyl glutarate and in the presence of an activating solvent of the formula (IIIb)

$$R_2N\text{—}CO\text{—}O\text{—}R \qquad (IIIb)$$

in which the R radicals are $C_1$–$C_6$-alkyl groups, 2 of which R groups are interconnected to form a cyclic carbamate having 5 to 7 ring members and one of the R groups is a $C_1$–$C_6$-alkyl group on the nitrogen atom, which solvent (IIIb) can also carry up to 2 $C_1$–$C_2$-alkyl groups on the ring.

4. The process of claim 3, wherein the alkanol (II) used as methanol or ethanol.

* * * * *

UNITED STATES PATENT AND TRADEMARK OFFICE
CERTIFICATE OF CORRECTION

PATENT NO.: 5,434,290

DATED: July 18, 1995

INVENTOR(S): STAHL et al.

It is certified that error appears in the above-identified patent and that said Letters Patent is hereby corrected as shown below:

Column 6, claim 4, line 2, delete "as" and substitute --is--.

Signed and Sealed this

Twenty-sixth Day of September, 1995

Attest:

BRUCE LEHMAN

*Attesting Officer*  *Commissioner of Patents and Trademarks*